US00PP13209P3

(12) United States Plant Patent

Craig et al.

(10) Patent No.: US PP13,209 P3

(45) Date of Patent: Nov. 12, 2002

(54) REGAL PELARGONIUM PLANT NAMED 'CAMELOT'

(75) Inventors: Richard Craig, State College, PA (US); Marietta Loehrlein, Macomb, IL (US)

(73) Assignee: Penn State Research Foundation, University Park, PA (US)

( * ) Notice: Subject to any disclaimer, the term of this patent is extended or adjusted under 35 U.S.C. 154(b) by 56 days.

(21) Appl. No.: 09/781,528

(22) Filed: Feb. 9, 2001

(65) Prior Publication Data

US 2002/0112271 P1 Aug. 15, 2002

(51) Int. Cl.[7] ..... A01H 5/00

(52) U.S. Cl. ..... Plt./331

(58) Field of Search ..... Plt./331

*Primary Examiner*—Bruce R. Campell

*Assistant Examiner*—Annette Para

(74) *Attorney, Agent, or Firm*—Webb Ziesenheim Logsdon Orkin & Hanson, P.C.

(57) ABSTRACT

A new and distinct regal geranium plant with an abundance of purple colored flowers with a distinct dark purple blotch above medium green foliage. The new cultivar is compact, self-branching, and early flowering.

2 Drawing Sheets

BOTANICAL CLASSIFICATION

*Pelargonium×domesticum* cultivar Camelot.

BACKGROUND OF THE INVENTION

The present invention comprises a new and distinct cultivar of *Pelargonium×domesticum* known by the varietal name 'Camelot' (Oglevee No. 234, Breeder No. 95-9-2). The cultivar was developed from an organized, scientifically designed breeding program conducted at the Department of Horticulture, The Pennsylvania State University, University Park, Pa. 16802. The breeding program was designed to create new regal Pelargonium genotypes with clear, bright flower colors, excellent propagation characteristics, compact growth habit, predictable and consistent flowering response and good post-production quality. The cross-pollination was done on Apr. 12, 1995. The pistillate parent of this new cultivar is 'Duchess' (U.S. Plant Pat. No. 8,074). The staminate parent (Breeder No. 93-11-5) was produced from prior selections developed at The Pennsylvania State University. The pedigree of the staminate parent includes the patented varieties 'Splendor' and 'Fantasy' (U.S. Plant Pat. Nos. 7,656 and 7,538, respectively) and other unpatented varieties and appears in FIG. 2. The new cultivar was first asexually reproduced on Sep. 9, 1996 by cuttings in University Park, Pa. The new cultivar has been trial and field tested at Connellsville, Pa. and has been found to retain its distinctive characteristics through successive propagations.

The cultivar, when grown in a glass greenhouse in Connellsville, Pa. using natural light and temperatures of 60° F. night and 68° F. day, has a response time of thirteen weeks from a rooted cutting to flowering in a 6 inch pot. The response time was determined on plants grown in soilless media employing constant fertilizer with 150–200 parts per million of nitrogen and potassium in full light.

DESCRIPTION OF THE DRAWINGS

FIG. 1 is a photographic drawing illustrating the new cultivar, with the color being as nearly true as is possible with color illustrations of this type.

DESCRIPTION OF THE PLANT

Figure 2:
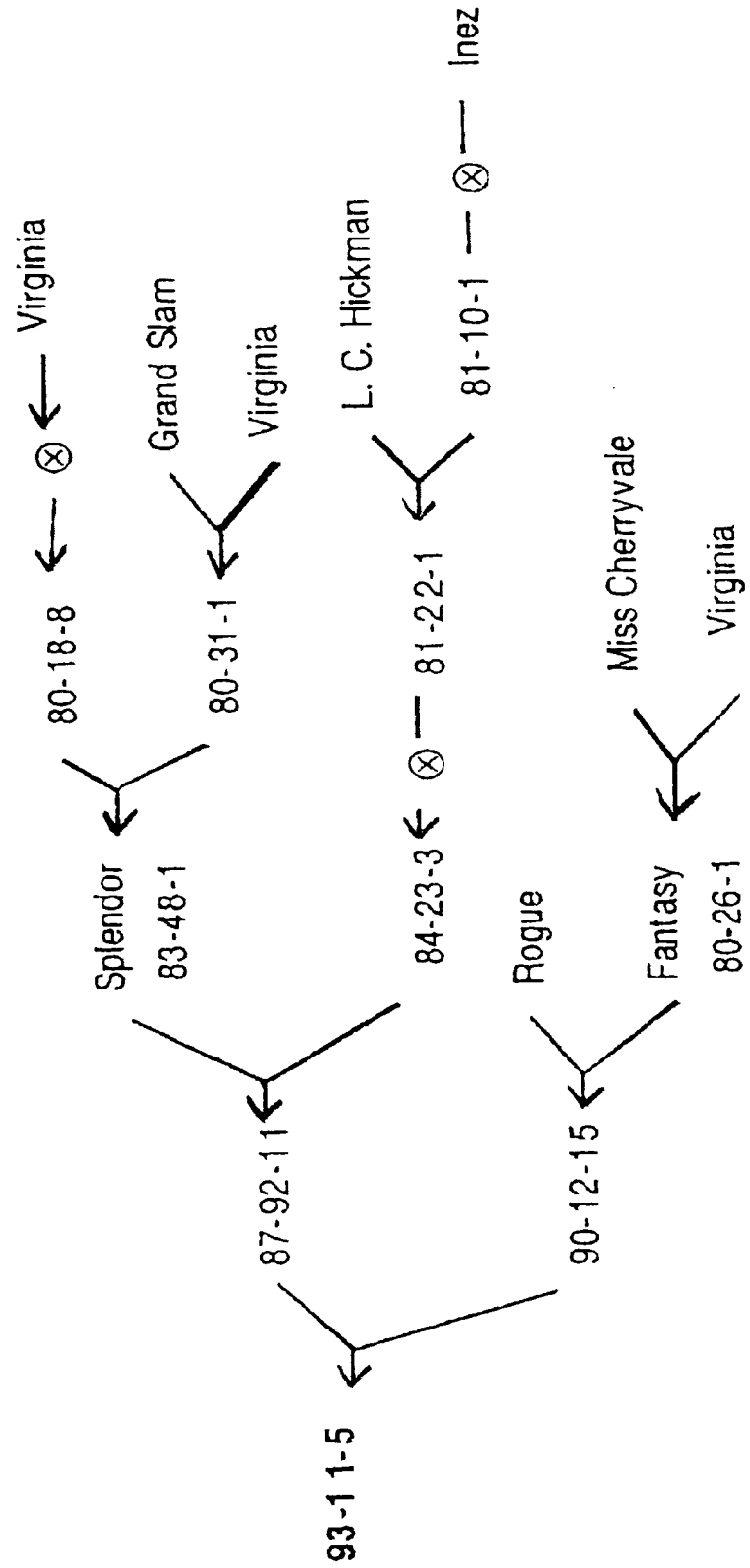
FIG. 2 is a flow chart of the pedigree of the staminate parent of the new cultivar.

The following detailed description sets forth the characteristics of the new cultivar. The data which defines these characteristics were collected from asexual reproductions carried out by Oglevee, Ltd. in Connellsville, Pa. The color readings were taken indoors under 200–220 foot candles of fluorescent cool white light. Color references are primarily to The R.H.S. Colour Chart of The Royal Horticultural Society of London.

PLANT

Classification:
- *Botanical.*—*Pelargonium×domesticum.*
- *Commercial.*—Regal pelargonium.

Form: Medium mound.

Height: 18.0–21.0 cm from media to top of foliage.

Growth: Upright, free basal branching.

Strength: Does not require artificial support.

Foliage: Zonation not present; stalked leaf attachment.

Rooting time: Roots visible to outside of artifical dirt plug in 14–21 days.

Leaves:
- *Size.*—Length: 5.4–8.2 cm. Width: 8.0–11.0 cm.
- *Shape.*—Reniform; truncate base.
- *Margin.*—Serrated; lobed.
- *Texture.*—Rough; pubescent.
- *Color.*—Upper surface: Yellow-Green Group 146A. Lower surface: Yellow-Green Group 146C.
- *Ribs and veins.*—Venation: Palmate. Color: Yellow-Green Group 146D.

Petioles:
- *Color.*—Yellow-Green Group 146D.
- *Length.*—4.6–6.0 cm.

Stem:
- *Color.*—Yellow-Green Group 146D.
- *Internode length.*—2.0–3.0 cm.

THE BUD

Shape when just showing color:
*Overall.*—Elliptical cluster.
*Individual bud.*—Elliptical.
Size when just showing color:
*Overall.*—4.0–5.5 cm.
*Individual bud.*—3.0–3.5 cm.
Number of buds per cluster: 6–12.

INFLORESCENCE

Blooming habit: Continuous flowering; large florets forming full flower heads.
Overall size: 8.5–12.0 cm.
Borne: Floret on pedicel; pedicel on peduncle.
Florets:
*Form.*—Slightly cupped; some ruffling on petal margins.
*Number of florets per umbel.*—5–7.
*Size.*—Length: 4.0–4.5 cm. Width: 5.5–6.5 cm wide. Depth: 3.5–4.2 cm from base of floret to edge of petals.
*Petals.*—Color: Upper surface: Purple Group 78B at outer edge darkening to Red-Purple Group 74B at outer edge of blotch. Eye gradually gets darker toward center of petal progressing to the darkest color of Greyed-Purple Group 187A. Toward base of petal, blotch and veining is Red-Purple Group 71A. Base of petal is White Group 155D. Lower surface: Purple group 75D with specks of Purple Group 78C and blotch of Red-Purple Group 74A showing through. Eye: Red-Purple Group 74B at outher edge progressing toward center of petal to dark purple, almost black, Greyed-Purple Group 187A. Veining of various shades ranging from Red-Purple Group 71A to Greyed-Purple Group 187A is present. Eye is present on each petal of floret, though is larger on upper two petals. Shape: Obovate. Size: Length: 4.0 cm. Width: 2.5–3.0 cm. Margin: Entire. Number per floret: 5. Texture: Smooth, velvety.
Tonality from a distance: Medium green mound of foliage topped by an abundance of purple flowers with a distinct dark purple blotch.
Petaloids:
*Quantity.*—If present, 1–2 per floret.
*Shape.*—Irregular; one of the lower petals is cut part way through giving a ruffled appearance. It is not cut the whole way down the petal but is actually part of the lower petal. This trait is somewhat consistent and is noticed on most of the florets.
*Color.*—Same as petals.
Pedicel:
*Length.*—2.5–3.0 cm.
*Color.*—Yellow-Green Group 146C.
Peduncle:
*Length.*—4.0–5.0 cm.
*Color.*—Yellow-Green Group 146B.
Disease/pest resistance: No unusual susceptibility to diseases or pests has been noted to date.
Lasting quality: This cultivar flowers continually but the umbels will last 14 to 21 days depending on conditions.

REPRODUCTIVE ORGANS

Stamens:
*Anthers.*—3.0 mm long.
*Filaments.*—Length: 2.0–2.5 cm. Color: Green-White Group 157D at base with Red-Purple 62D at tips. Pollen: Greyed-Orange Group 173B.
Pistils:
*Number.*—One.
*Length.*—2.0–2.5 cm.
*Stigma.*—Number: One; 5–6 parted. Color: Greyed-Purple Group 187C.
*Style.*—Length: 1.5–1.7 cm. Color: Greyed-Purple Group 187C.
*Ovaries.*—Completeness: Superior. Pubescence: Very pubescent. Length: 5–7 mm. Width: 3–4 mm. Color: Yellow-Green Group 147C.
Fruit: None observed.

GENERAL CHARACTERISTICS

1. This new variety is similar in color to the current market variety 'Jane' (U.S. Plant Pat. No. 9,893) in color.

2. Cutting production is comparable to 'Jane'.

3. Rooting speed is improved over 'Jane' by 7 days. Under optimal conditions rooting occurs in 14 days after sticking.

4. Plant habit is greatly improved as 'Jane' is very vegetative whereas 'Camelot' is not as vegetatively vigorous.

5. Amount of umbels and flowers/umbel is improved over 'Jane' by 30%.

6. Earlier to flower than 'Jane' by one to two weeks depending on conditions.

7. Flowering time is also improved over 'Jane' from 3–4 weeks to 6–8 weeks of continuous flowering.

8. Outdoor growth and flowering in central Pennsylvania is greatly improved over 'Jane'.

I claim:

1. A new and distinct variety of geranium plant substantially as shown and described.

* * * * *

UNITED STATES PATENT AND TRADEMARK OFFICE

CERTIFICATE OF CORRECTION

PATENT NO. : PP 13,209 P2
DATED : November 12, 2002
INVENTOR(S) : Richard Craig et al.

It is certified that error appears in the above-identified patent and that said Letters Patent is hereby corrected as shown below:

Column 1,
Line 1, before "BOTANICAL CLASSIFICATION", insert:
-- STATEMENT REGARDING FEDERALLY SPONSORED RESEARCH This invention was made with the support of the United States Government under USDA Hatch Act Project No. PEN03569. The Government has certain rights in the invention. --

Signed and Sealed this

Twelfth Day of August, 2003

JAMES E. ROGAN
*Director of the United States Patent and Trademark Office*